United States Patent [19]

Schrider

[11] 4,006,236
[45] Feb. 1, 1977

[54] SUBSTITUTED OCTAHYDROPHENANTHRIDINE PESTICIDES

[75] Inventor: Michael Stanley Schrider, South Bound Brook, N.J.

[73] Assignee: American Cyanamid Company, Stamford, Conn.

[22] Filed: Aug. 4, 1975

[21] Appl. No.: 601,732

[52] U.S. Cl. .............................................. 424/258
[51] Int. Cl.$^2$ .......................................... A01N 9/22
[58] Field of Search .............. 424/258; 260/283 CF

[56] References Cited

UNITED STATES PATENTS

| 3,311,631 | 3/1967 | Chafetz et al. | 260/283 CF |
| 3,336,313 | 8/1967 | Chafetz et al. | 260/283 CF |
| 3,349,092 | 10/1967 | Chafetz et al. | 260/283 CF |
| 3,408,351 | 10/1968 | Chafetz et al. | 260/283 |

OTHER PUBLICATIONS

Chemical Abstracts, vol. 41 (1947), p. 2449d.

*Primary Examiner*—V. D. Turner
*Attorney, Agent, or Firm*—Neal O. Willmann

[57] ABSTRACT

This invention discloses a method for the treatment and control of ectoparasites such as ixodid ticks and fleas either by a topical application to the larvae, nymphs, or adults of said parasites or by systemic administration to the host with an ectoparasiticidally effective amount of a substituted octahydrophenanthridine compound.

18 Claims, No Drawings

SUBSTITUTED OCTAHYDROPHENANTHRIDINE PESTICIDES

BACKGROUND OF THE INVENTION

The active compounds of this invention are heterocyclic compounds which may be represented by the following formula:

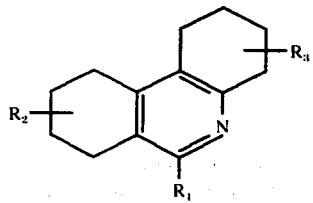

wherein $R_1$ is a member selected from the group consisting of $C_1$–$C_{10}$ alkyl straight chain or branched, $C_2$–$C_7$ alkenyl straight chain or branched, $C_3$–$C_8$ alkynyl straight chain or branched, $C_3$–$C_7$ cycloalkyl. $R_2$ and $R_3$ can be either hydrogen or methyl.

Substituted octahydrophenanthridines, and analogues thereof have been described and claimed by H. Chafetz et al. in U.S. Pat. Nos. 3,311,631; 3,336,313; 3,349,092; and 3,408,351 as corrosion inhibitors in oil and gas wells and also with pickling acids. The cited patents, however, do not suggest any pesticidal activity nor could the acaricidal and siphonaptericidal activity exhibited by the substituted octahydrophenanthridines claimed in the present application be anticipated therefrom.

A large number of references can be found in the published literature relating to substituted phenanthridines and their use as trypanocidal and antibacterial agents, e.g., (Chem. Abst. 41: 2449 g; 41: 2465 g; 49: 429 i); as anti-virals, (Chem. Abst. 47: 8829 b); as antidepressants, (Chem. Abst. 40: 871–882; 71: 49979 f) and as antispasmodics, (Chem. Abst. 46: 2548 a). Some of these references mention di-, tetra-, and hexahydro- analogues as having some of the above-mentioned biological and pharmacological activities, but neither of the references suggests nor anticipates ectoparaciticidal activity.

SUMMARY OF THE INVENTION

This invention discloses methods of treatment for various ectoparasites by the use of 6-substituted 1,2,3,4,-7,8,9,10-octahydrophenanthridines of the following formula:

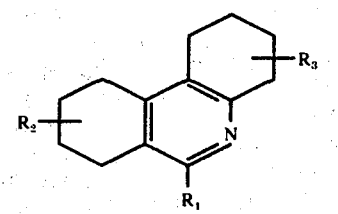

wherein $R_1$ is a member selected from the grouping consisting of $C_1$–$C_{10}$ alkyl straight chain or branched, $C_2$–$C_7$ alkenyl straight chain or branched, $C_3$–$C_8$ alkynyl straight chain or branched, $C_3$–$C_7$ cycloalkyl, and $R_2$ and $R_3$ are hydrogen or methyl.

DESCRIPTION OF THE PREFERRED EMBODIMENT

Ectoparasites of homothermic companion and farm animals are the cause of significant economic losses in animal agriculture, and may in addition, have a significant role as vectors for various diseases transmissible to man and other animals. Control of these pests is, therefore, highly desirable.

The present invention relates to a method for the control of Acarina such as Boophilus, Amblyomma, Anocentor, Dermacentor, Ixodes, Haemaphysalis, Hyalomma, Rhipicentor, Morgaropus, Rhipicephalus, Argas, Otobius and Ornithodoros, and of ectoparasites such as fleas in the larval, nymph and adult stages. The method of the present invention is particularly useful for the control of ixodid ticks such as Boophilus and Amblyomma and/or fleas parasitizing homothermic farm animals, such as cattle, swine, sheep and goats; poultry such as chickens, turkeys and geese, fur bearing animals such as mink, foxes, chinchillas, rabbits and the like; and companion animals such as dogs and cats.

To control Acarina, particularly ixodid ticks such as Amblyomma and Boophilus, and insect pests such as fleas, infesting the above said companion, farm and fur bearing animals, an ectoparasiticidally effective amount of a substituted octahydrophenanthridine compound wherein $R_1$, $R_2$, and $R_3$ are as defined above, is applied to the larvae, nymphs, or adults of said Acarina or insect pests or to their hosts or habitat.

Substituted octahydrophenanthridines also possess systemic pesticidal activity and may be administered to the above homothermic companion and farm animals orally or parenterally at a rate of from 1 mg./kg. to 500 mg./kg. active compound and preferably at a rate of from 5 mg./kg. to 30 mg./kg. active compound per animal body weight.

Substituted octahydrophenanthridines may be conveniently prepared by a synthetic route described by Chafetz et al. in the "General Papers presented to the Division of Petro Chemicals" Am. Chem. Soc., Boston Meeting, April, 1972, pages B 27 to 37. The synthetic route described below is a slightly modified version of the route described in the above said papers:

2-(1-Cyclohexenyl)cyclohexanone is reacted with an amide of the formula: $R_1$-$CONH_2$, wherein $R_1$ is as defined above, in an aprotic solvent such as toluene or the like, at reflux from about 10 to 24 hours in the presence of a strongly acidic resin of p-toluene sulfonic acid used as a catalyst. The resulting enamide (II) is recovered and treated with excess $POCl_3$ to affect ring closure to the desired octahydrophenanthridine compound. The above reaction sequence may be graphically illustrated as follows:

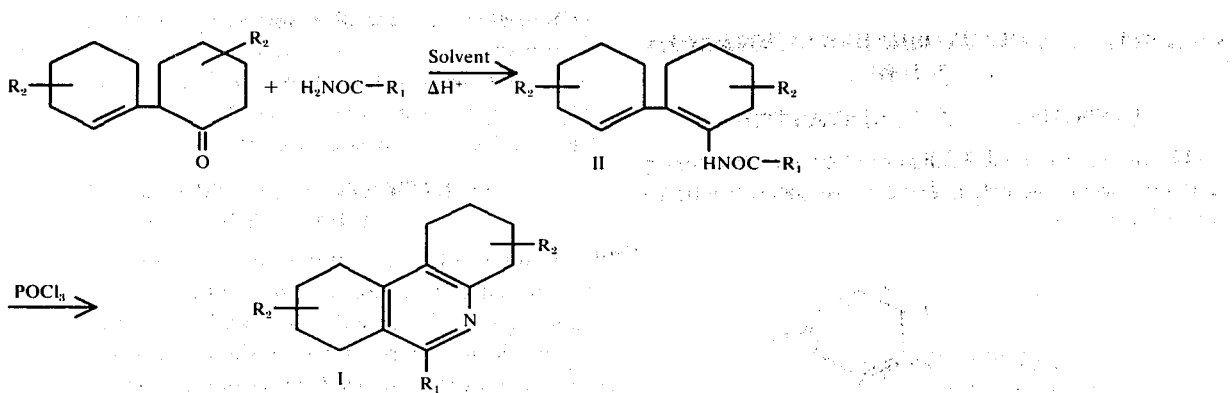

wherein $R_1$ and $R_2$ are as defined above. Standard laboratory procedures such as extractions, vacuum distillations, chromatography and the like may be employed to purify both the intermediate enamide II and the final product, if so desired.

As stated before, control of the above-mentioned Acarina and especially ixodid ticks and of ectoparasites such as fleas, can be effected by applying a pesticidal amount of a substituted octahydrophenanthridine compound to the larvae, nymphs of said ticks or fleas; or their hosts, habitat or food and water of the animals infested with said pest may be treated with a pesticidal amount of a substituted octahydrophenanthridine compound. The dosages at which these compounds are applied may be from 0.01% to 5.0% and preferably from 0.01% to 1.0%, said dosages to be determined within the above specified ranges by the degree of control desired, and are concomitant with good animal husbandry practices.

Substituted octahydrophenanthridines may be formulated as solutions, emulsifiable concentrates, wettable powders, dusts and dust concentrates. Solutions, emulsifiable concentrates and wettable powders are especially useful and convenient formulations since they may be diluted with water, or another suitable solvent such as lower aliphatic ketones, lower aliphatic alcohols, keto alcohols such as diacetone alcohol, various esters and the like in situ, and applied to the larvae, nymphs and adult insect pests; or the hosts, habitat or food and water of the animals infested with said pests may be treated topically with the prepared dilute sprays containing the active component in the above defined concentration.

For oral or parenteral use, said pesticidally active octahydrophenanthridine compounds may be formulated as boluses, tablets, pellets, pastes, oral drenches, injectables and the like, using pharmaceutically acceptable carriers, diluents, solvents and the like.

Dusts and dust concentrations may be prepared by grinding and blending together an inert solid diluent such as attapulgite, bentonite, diatomaceous earth, fullers earth, kaolin and the like with the active compound, if the latter is a solid. If the active compound is a liquid, it or a solution of it may be sprayed on the inert carrier and then thoroughly blended with said carrier. Dusts usually contain from about 1% to 15% by weight of active ingredient, whereas dust concentrates may contain 15% to 85% by weight of active ingredient.

Wettable powders are prepared as the above dust concentrates except that about 1% to 5% of a dispersing agent such as the calcium salt of a polymerized alkyl aryl sulfonic acid, sodium lignosulfonate or sodium salt of condensed naphthalene sulfonic acid and about 1% to 5% by weight of a surfactant, such as polyoxyethylated vegetable oil, alkyl phenoxy polyoxyethylene ethanol, sodium alkyl naphthalene sulfonate is also blended with the formation.

Solutions may be formulated with organic solvents such as lower aliphatic ketones, lower aliphatic alcohols, keto alcohols such as diacetone alcohol, various esters, cyclohexanone, aliphatic and aromatic hydrocarbons and petroleum distillates having at least 85% aromatic content, and may be applied directly as sprays.

Emulsifiable concentrates may be prepared by dissolving or dispersing about 15% to 75% by weight of active compound in a suitable solvent or carrier such as the solvents described above, and incorporating about 10% by weight of a surfactant or blend of surfactants. Surfactants, such as alkyl polyoxyethylene ethers, polyoxyethylene (20) sorbitan monolaurate, polyoxyethylene (20) sorbitan monooleate, alkyl aryl polyglycol ethers, condensates of polyoxy ethylenes, alkyl aryl sulfonates and the like are preferred singly or in combination. These concentrates are usually also diluted with water for application.

The present invention is further illustrated by the following examples which are not to be taken as being limited thereto. Unless otherwise indicated, all parts and percentages are by weight in the following examples, as well as in the claims and the discussion above.

EXAMPLE 1

Preparation of
N-[2-(1-cyclohexen-1-yl)-1-cyclohexen-1-yl]hexanamide 2-(1-Cyclohexenyl)cyclohexanone (17.8 g., 0.1 mole), hexanamide (11.5 g., 0.1 mole), 5.0 g. of a highly acidic resin, Amberlyst 15, and toluene (150 ml) are mixed, stirred and heated at reflux for 16 hours. The water formed in the course of the reaction is azeotroped from the reaction mixture. The hot solution is decanted from the Amberlyst catalyst, the catalyst washed with toluene (200 ml.), and the toluene fractions are combined. Pentane (300 ml.) is added to the toluene solution, the mixture chilled in ice and filtered to remove 3.65 g. of unreacted hexanamide. The orange filtrate is stripped to yield 24 g. of crude product, an oil.

The crude is eluted with methylene dichloride on a dry silica column to yield 6.0 g. of 85% pure product. A second elution on a dry silica column yields 3.3 g. pure product. The structure is confirmed by infra red and nuclear magnetic resonance.

Additional product may be recovered from the mother liquor.

EXAMPLE 2

Preparation of 1,2,3,4,7,8,9,10-Octahydro-6-n-pentylphenantridine 1.2 Grams of crude enamide of Example 1 and 20 ml. of $POCl_3$ are mixed and heated at reflux for 1 hour.

The $POCl_3$ is then evaporated, the residue stirred with water and hexane and saturated sodium bicarbonate solution added until the aqueous phase becomes alkaline. The hexane phase is then dried and concentrated. The resulting yellow oil is stirred with 6N hydrochloric acid and the acid solution washed twice with hexane. The aqueous, acidic solution is made alkaline with 50% sodium hydroxide while being kept cold with ice, and extracted with hexane. The hexane solution is washed with saturated salt solution, dried and concentrated to yield 0.44 g. of a yellow oil, identified by infra red and thin layer chromatography as very pure product.

EXAMPLE 3

By the procedures of Examples 1 and 2 the following 6-substituted 1,2,3,4,7,8,9,10-octahydrophenanthridines, all of which are oils or waxy solids at ambient temperature, are prepared and identified by microanalyses, infra red, nuclear magnetic resonance and thin layer chromatography:

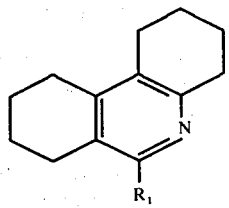

$R_1$: $-CH_3$, $-C_2H_5$, $-C_3H_7$, $-CH(CH_3)_2$, $-C_4H_9$, $-CH_2-CH(CH_3)_2$, $-CH_2-CH_2-CH(CH_3)_2$, $-CH_2-C(CH_3)_3$, $-n-C_6H_{13}$, $-n-C_7H_{15}$, $-n-C_{11}H_{23}$, $-n-C_{17}H_{35}$,

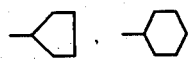

Additional compounds wherein $R_1$ is $CH_2=CH-$, $$CH_2=C-, \atop CH_3$$

$(CH_3)_2C=CH-$,   $CH_3-CH=CH-$,
$CH_3(CH_2)_3-CH=CH-$,   $CH_3(CH_2)_5-CH=CH-$,
$CH\equiv C-CH_2-$,   $CH_3-C\equiv C-CH_2-$,
$CH_3(CH_2)_2-C\equiv C-CH_2-CF_3$,

may be prepared by the above referred to procedures.

EXAMPLE 4–13

Suppression of Fecundity and Chemosterilant Effect in Ixodidae

The efficacy of the compounds of the present invention for suppression of fecundity in ticks is demonstrated in the following tests wherein engorged adult female *Boophilus microplus* ticks which have dropped from cattle are collected and used for testing.

The compound to be tested is dissolved in a 35% acetone/65% water mixture in sufficient amount to provide 500 ppm, 1,000 ppm and 2,000 ppm of compound in the test solution. Ten ticks per treatment are used and they are immersed in test solution for 3 to 5 minutes, then air dried for 5 minutes and removed and placed in dishes and held in incubators for 2 to 3 weeks at 28° C. Counts of ticks laying eggs are then made and recorded. Eggs which were laid are placed in containers and kept for one month to observe hatching and to determine chemosterilant effect. For each test, ten nonresistant ticks (S strain) as well as ten ethion-resistant (M strain) and ten dioxathion-resistant ticks (D strain) are used since the latter two are among the most difficult of their kind to control. Results of these tests are given in Table I below. The rating system used for each tick is as follows:

| Rating System | |
|---|---|
| Result | Score |
| No oviposition | 4 |
| Partial oviposition, no hatch | 3 |
| Total oviposition, no hatch | 2 |
| Partial oviposition, viable eggs | 1 |
| Normal oviposition and hatch | 0 |

The rating system is based on the summation of scores from all ticks regardless of the dose rate or strain of ticks tested. Using this rating system the best score possible would be 360, or 90 (the total number of ticks used) × 4 (the highest score). The efficacy is reported as percent of the best possible score.

Table I

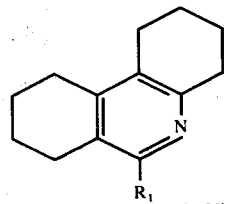

| Example | $R_1$ | In Vitro Adult Boophilus microplus Efficacy (%) |
|---|---|---|
| 4 | n-$C_5H_{11}$*+ | 97 |
| 5 | $CH_3$ | 76 |
| 6 | $C_2H_5$ | 30 |
| 7 | n-$C_{17}H_{35}$ | 14 |
| 8 | n-$C_3H_7$ | 54 |
| 9 | $-CH_2CH(CH_3)_2$ | 53 |
| 10 | i-$C_3H_7$ | 17 |
| 11 | n-$C_4H_9$ | 49 |
| 12 | n-$C_5H_{11}$ | 97 |
| 13 | $-CH_2CH_2-CH(CH_3)_2$ | 66 |
| 14 | $-CH_2C(CH_3)_3$ | |
| 15 | 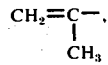 | 91 |
| 16 | n-$C_6H_{13}$ | 87 |
| 17 | 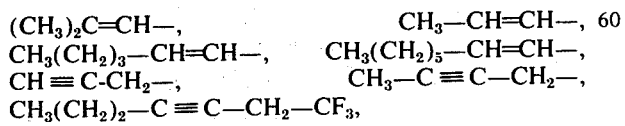 | 15 |
| 18 | n-$C_7H_{15}$ | 81 |

Table I-continued

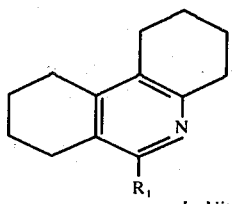

| Example | R₁ | In Vitro Adult Boophilus microplus Efficacy (%) |
|---|---|---|
| 19 | n-C₁₁H₂₃ | 3 |
| 20 | *The HCl Salt | 30 |
| 21 | + The Phenanthridine analog | 8 |

EXAMPLE 22

Larvicidal Activity

The effective control of Acarina larvae is demonstrated in the following tests with larvae of *Boophilus microplus*, a one-host tick which remains on a single host through its three life stages, i.e., larva, nymph and adult. In these tests, a 10% acetone/90% water mixture contains from 1.0 to 100 ppm of 6-n-pentyloctahydrophenanthridine. Twenty larvae are enclosed in a pipet sealed at one end with a gauze material and solution containing the test compound is then drawn through the pipet with a vacuum hose simulating a spray system. The ticks are then held for 48 hours at room temperature and 80% relative humidity and mortality is determined. The following data are obtained:

| Concentration ppm | 48 Hour Mortality (%) |
|---|---|
| 33 | 100 |
| 10 | 0 |

EXAMPLE 23

Cattle Spray Trial

An experimental emulsifiable concentrate is prepared by blending: 6-n-pentyl-1,2,3,4,7,8,9,10-octahydrophenanthridine: 25% w/w, polyoxyethylene alkyl aryl ether-alkyl aryl sulfonate blend 9.0% w/w, (Atlox 3403), polyoxyethylene ether polyoxyethylene glyceride alkyl aryl sulfonate blend 6.0% w/w, (Atlox 3404) and a petroleum distillate having at least 85% aromatic content 60% w/w (Panasol An-2) the above emulsifiable concentrate is diluted with water to yield spray solutions at 1,000 ppm, 1,500 ppm and 2,500 ppm concentrations of active component.

Experimental Animals

Holstein heifers, 6 to 12 months old, are experimentally infested twice a week for 4 weeks before treatment and for three more weeks afterwards, with approximately 5,000 unfed *Boophilus microplus* tick larvae. The cattle are maintained on native pastures throughout the experiment. Heavy infestations of all stages of *Boophilus microplus* are found on the day of treatment. The tick larvae are from a strain that is susceptible to all organophosphorus ixodicides.

At each test concentration level 5 cattle are sprayed, each with 12 liters of emulsion delivered with a hand-directed spray wand connected to a pump that delivers 12 liters of spray per minute at a pressure of 21 kg/cm².

Assessment of Results

Tick counts on the left side of each animal are made before and after treatment and the results are calculated as percent survival. The data are given in the Table II below:

Table II

| Mean Percent Survival of Female Ticks (4.5 mm - 8.0 mm) on Cattle Sprayed with 6-n-Pentyl-1,2,3,4,7,8,9,10-octahydrophenanthridine | |
|---|---|
| Dose Level (ppm) | Mean Percent Survival 10–15 Days |
| 1000 | 18.7 |
| 1500 | 9.9 |
| 2500 | 4.7 |

EXAMPLE 24

Siphonaptericidal Activity

The siphonaptericidal efficacy of the compounds of this invention is demonstrated by the following test wherein 6-n-pentyl-1,2,3,4,7,8,9,10-octahydrophenanthridine is utilized as the active ingredient. Ten adult fleas of the species *Ctenocephalides felis* are sprayed for 30 seconds with a 10% acetone/90% water mixture containing 100 ppm of test compound. After this treatment the fleas are maintained for 48 hours at room temperature and 80% relative humidity. At the end of this period, mortality counts are made. With the above-named compound, representative of the compounds disclosed, 100% mortality is obtained.

EXAMPLE 25

Guinea Pig Spray Trial

The back of an albino guinea pig is shaved with a No. 40 animal clipper blade. One 2 inch spud gasket with the base ground down to ⅛ inch is glued to the back of the guinea pig with 3M brand super weatherstrip adhesive, part No. 8001. Five male and 5 female adult *Dermacentor variabilis* or *Rhipicephalus sanguineus* are placed in each capsule and sprayed 3 days later with a given concentration of the candidate compound. 2 ml. of the solution is sprayed into the spud gasket area and on the ticks within that area. The ticks are observed daily for mortality. Engorged females are collected and held in an incubator at 27° C. and 80% + R.H. for oviposition. Eggs are collected from each female after 3 weeks in the incubator and placed in a vial for hatching.

Percent hatch compared to the control is measured after an additional 3-week period.

Unless otherwise specified, a ⅓ acetone- ⅔ water solution of the compound is used in this test. Tables III and IV show the data obtained, the compound used in the test and the formulation employed.

Table III

| In Vivo Spray Trial with 6-n-Pentyl-1,2,3,4,7,8,9,10-octahydrophenanthridine | | | |
|---|---|---|---|
| Tick Adults | Application Rate: ppm | No. of Engorged Female Ticks | % Hatch |
| *Dermacentor variabilis* | Control | 4 | 90 |
| | 500 | 5 | 90 |
| | 2000 | 4 | 50 |
| *Rhipicephalus* | Control | 5 | 70 |

Table III-continued

In Vivo Spray Trial with 6-n-Pentyl-1,2,3,4,7,8,9,10-octahydrophenanthridine

| Tick Adults | Application Rate: ppm | No. of Engorged Female Ticks | % Hatch |
|---|---|---|---|
| sanguineus | 500 | 4 | 70 |
|  | 2000 | 3 | 10 |

Table IV

In Vivo Spray Trial with 6-n-Pentyl-1,2,3,4,7,8,9,10-octahydrophenanthridine, formulated as an Experimental Emulsifiable Concentrate (Same as that of Example 15)

| Tick Adults | Application Rate: ppm | % Female Ticks Alive | % Hatch |
|---|---|---|---|
| Dermacentor variabilis | Control | 100 | 75 |
|  | 2500 | 70 | 65 |
|  | 5000 | 80 | 50 |
|  | 10,000 | 80 | 10 |
| Rhipicephalus sanguineus | Control | 100 | 75 |
|  | 2500 | 80 | 0 |
|  | 5000 | 40 | 0 |
|  | 10,000 | 0 | 0 |

I claim:

1. A method for the control of insects and Acarina comprising, contacting the larvae, nymphs or adults of said insects and Acarina with an insecticidally and Acaricidally effective amount of a compound represented by the following formula:

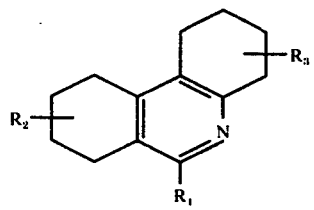

wherein $R_1$ is a member selected from the group consisting of $C_1$–$C_{10}$ alkyl straight chain or branched, $C_2$–$C_7$ alkenyl straight chain or branched, $C_3$–$C_8$ alkynyl straight chain or branched, and $C_3$–$C_7$ cycloalkyl, and $R_2$ and $R_3$ are hydrogen or methyl.

2. The method according to claim 1, wherein $R_1$ is a member from the group consisting of $C_1$–$C_6$ alkyl straight chain or branched, and $C_5$–$C_6$ cycloalkyl, and $R_2$ and $R_3$ are as defined above.

3. The method according to claim 1, wherein said compound is 6-n-pentyl-1,2,3,4,7,8,9,10-octahydrophenanthridine.

4. The method according to claim 1, wherein said compound is 6-methyl-1,2,3,4,7,8,9,10-octahydrophenanthridine.

5. The method according to claim 1, wherein said compound is 6-i-butyl-1,2,3,4,7,8,9,10-octahydrophenanthridine.

6. The method according to claim 1, wherein said compound is 5-butyl-1,2,3,6,7,8-hexahydrodicyclopenta[b,d]pyridine.

7. The method according to claim 1, wherein said ectoparasites are ixodid ticks.

8. The method according to claim 1, wherein said ectoparasites are fleas.

9. The method according to claim 1, wherein said compound is applied at a rate from about 0.01% to about 5.0%

10. The method according to claim 1, wherein said compound is applied at a rate from about 0.01% to about 1.0%

11. A method for the control of insects and Acarina comprising, introducing orally or parenterally into the body of farm animals or a companion animal selected from the group consisting of cats and dogs an insecticidally and Acaricidally effective amount of a compound of the following formula:

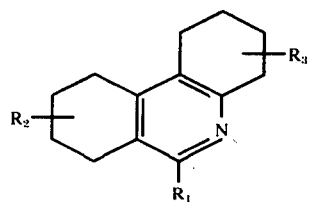

wherein $R_1$ is a member selected from the group consisting of $C_1$–$C_{10}$ alkyl straight chain or branched, $C_2$–$C_7$ alkenyl straight chain or branched, $C_3$–$C_8$ alkynyl straight chain or branched, and $C_3$–$C_7$ cycloalkyl, and $R_2$ and $R_3$ are hydrogen or methyl.

12. The method according to claim 11, wherein $R_1$ is a member selected from the group consisting of $C_1$–$C_6$ alkyl straight chain or branched, and $C_5$–$C_6$ cycloalkyl and $R_2$ and $R_3$ are as defined above.

13. The method according to claim 11, wherein said compound is administered orally or parenterally at a rate from about 1 mg./kg. to about 500 mg./kg. animal body weight.

14. The method according to claim 11, wherein said compound is administered orally or parenterally at a rate from 5 mg./kg. to about 30 mg./kg. animal body weight.

15. A method for the control of insects and Acarina comprising applying to the larvae, nymphs and adults of ticks or fleas or topically onto the body of farm animals or a companion animal selected from the group consisting of cats and dogs an insecticidally and Acaricidally effective amount of a compound of the following formula:

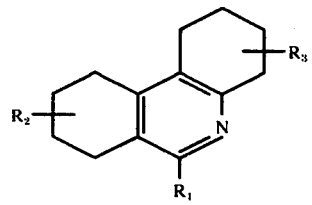

wherein $R_1$ is a member selected from the group consisting of $C_1$–$C_{10}$ alkyl straight chain or branched, $C_2$–$C_7$ alkenyl straight chain or branched, $C_3$–$C_8$ alkynyl straight chain or branched, and $C_3$–$C_7$ cycloalkyl, and $R_2$ and $R_3$ are hydrogen or methyl.

16. The method according to claim 15 wherein $R_1$ is a member selected from the group consisting of $C_1$–$C_6$ alkyl straight chain or branched, and $C_5$–$C_6$ cycloalkyl and $R_2$ and $R_3$ are as defined above.

17. The method according to claim 15, wherein said compound is applied topically at a concentration from about 0.01% to about 5.0%.

18. The method according to claim 15, wherein said compound is applied topically at a concentration from about 0.01% to about 1.0%.

* * * * *